United States Patent [19]

Arlt et al.

[11] 3,980,738
[45] Sept. 14, 1976

[54] PROCESS FOR THE PREPARATION OF (THIO)PHOSPHORIC (PHOSPHONIC) ACID ESTERS

[75] Inventors: Dieter Arlt, Cologne; Kurt Ley, Odenthal, both of Germany

[73] Assignee: Bayer Aktiengesellschaft, Leverkusen, Germany

[22] Filed: Mar. 12, 1975

[21] Appl. No.: 557,725

[30] Foreign Application Priority Data

Apr. 9, 1974  Germany............................ 2417143

[52] U.S. Cl.................. 260/971; 260/326.5 A; 260/332.1; 260/340.2; 260/399; 260/403; 260/939; 260/940; 260/941; 260/952; 260/956; 260/958; 260/963
[51] Int. Cl.². ..................... C07F 9/09; C07F 9/165
[58] Field of Search............. 260/971, 986, 326.5 A, 260/340.2, 403, 332.1, 399

[56] References Cited
UNITED STATES PATENTS 3,691,275   9/1972   Benghiat........................ 260/986 X

*Primary Examiner*—Richard L. Raymond
*Attorney, Agent, or Firm*—Burgess, Dinklage & Sprung

[57] ABSTRACT

A process for the preparation of a (thio)phosphoric(-phosphonic) acid ester of the formula

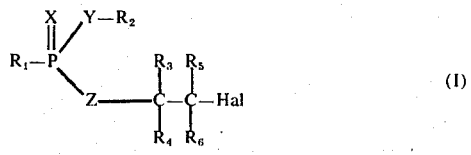

in which
 $R_1$ is a straight-chain or branched alkyl, alkylmercapto or alkoxy group with up to 8 carbon atoms,
 $R_2$ is alkyl with 1 to 8 carbon atoms optionally substituted by chlorine,
 $R_3$, $R_4$, $R_5$ and $R_6$ each independently is hydrogen or some other radical,
 X, Y and Z each independently is oxygen or sulfur, and
 Hal is chlorine or bromine,
which comprises reacting an olefin of the formula

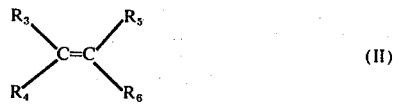

in a one-step process with a halogenating agent and a (thio)phosphoric(phosphonic) acid ester of the formula

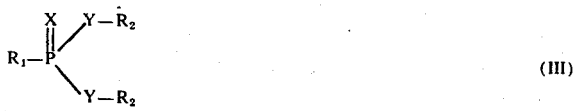

17 Claims, No Drawings

PROCESS FOR THE PREPARATION OF (THIO)PHOSPHORIC (PHOSPHONIC) ACID ESTERS

The present invention relates to a process for the preparation of certain (thio) phosphoric (phosphonic) acid esters which can be used as flameproofing agents and plasticizers in plastics.

It is known from U.S. Pat. No. 2,947,773 that O-β-chloroethylphosphoric acid esters can be obtained by reaction of phsophorus oxychloride with β-chloroethanol followed by reaction of the resulting intermediate product with an alcohol.

Furthermore, U.S. Pat. No. 3,453,348 describes a process for the preparation of esters of pentavalent phosphorus inter alia by condensation of (thio) phosphorous (phosphonous) acid esters with epoxides and halogenated hydrocarbons.

Finally, U.S. Pat. No. 3,206,495 discloses the preparation of O,O-dimethyl-O-[1,3-dichloro-2-propyl]-phosphoric acid esters by reaction of O,O-dimethylphosphoric acid ester chloride with epichlorohydrin in the presence of a catalyst.

However, these processes above all have the disadvantage that they are generally incapable of broad application since in many cases the starting materials required for the purpose are not available.

The present invention provides a process for the preparation of a (thio) phosphoric (phosphonic) acid ester of the general formula

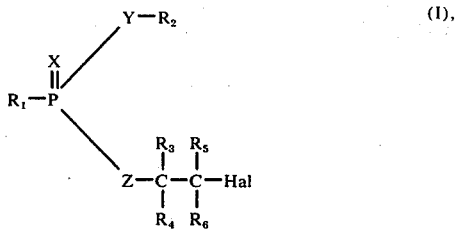

in which an olefin of the general formula

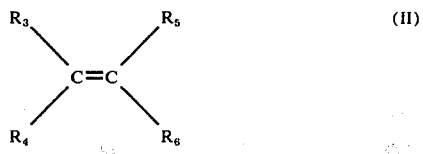

is reacted, in a one-step process, with a halogenating agent and a (thio) phosphoric (phosphonic) acid ester of the general formula

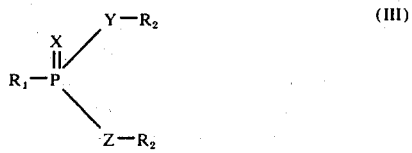

wherein $R_1$ is a straight-chain or branched alkyl, alkylmercapto or alkoxy group with up to 8 carbon atoms,
$R_2$ is alkyl with 1 to 8 carbon atoms optionally substituted by chlorine,
$R_4$ and $R_6$ each individually is hydrogen, $C_1$-$C_4$-alkyl or halogen,
X, Y and Z each independently is oxygen or sulfur,
Hal is chlorine or bromine, and
$R_3$ and $R_5$ each individually is hydrogen; halogen; a $C_1$-$C_{18}$-alkyl, acyloxy or $C_2$-$C_{12}$-alkenyl radical which can be substituted by halogen, an acyloxy or alkoxy group with up to 18 carbon atoms, isocyano, dichloroisocyano, chlorocarbonyl, cyano, chlorosulfonyl, a carbalkoxy group with up to 8 carbon atoms in the alkoxy moiety, or an optionally substituted carbamino group with up to 12 carbon atoms, phenyl; halogensubstituted phenyl; or $C_1$-$C_4$-alkyl-substituted phenyl;
$R_3$ and $R_5$ together form a 4 to 12-membered aliphatic or heterocyclic ring, or
$R_5$ may alternatively be chlorocarbonyl; cyano; a carbalkoxy or an optionally substituted carbamino group with up to 9 carbon atoms; an alkylcarbonyl, alkylsulfonyl, arylcarbonyl or arylsulfonyl group, each with up to 7 carbon atoms; or an aldehyde group.

Preferably, $R_1$ is alkyl with 1 to 6 carbon atoms (especially methyl), or alkoxy with 1 to 6 carbon atoms (especially methoxy or ethoxy, $R_2$ is alkyl with 1 to 6 carbon atoms (especially 1 or 2 carbon atoms) which is optionally substituted by chlorine, $R_3$ and $R_5$ each independently is hydrogen, fluorine, chlorine, bromine, acyloxy with up to 5 carbon atoms, alkyl or alkenyl with up to 6 carbon atoms (the three last-mentioned radicals optionally being substituted by chlorine, bromine, isocyano, dichloroisocyano, chlorocarbonyl, cyano, chlorosulfonyl, or carbalkoxy, acyloxy or alkoxy group containing up to 5 carbon atoms, especially up to 3 carbon atoms, or an alkylated carbamino group, and $R_4$, and $R_6$ are hydrogen or alkyl with up to 6 carbon atoms.

It is particularly preferred that the radicals $R_3$ and $R_4$ are fluorine or chlorine.

An alternative preferred meaning for $R_3$ and $R_5$ is that they form a 5-membered or 6-membered ring which in addition to carbon atoms can contain oxygen, a carbonyl group or a sulfone group as ring members; in this case, $R_4$ and $R_6$ are preferably each hydrogen, chlorine or methyl.

Other preferred meanings for $R_5$ are chlorocarbonyl, cyano, a carbalkoxy, mono-alkylated or di-alkylated carbamino group with up to 5 carbon atoms, an alkylcarbonyl or alkylsulfonyl group with up to 4 carbon atoms, or an arylsulfonyl or arylcarbonyl group with up to 7 carbon atoms; in this case, it is preferred that $R_3$, $R_4$ and $R_6$ should each be selected from hydrogen, chlorine, bromine and alkyl with up to 6 carbon atoms, although it is particularly preferred that at least one of them should be hydrogen.

It is especially preferred to prepare compounds of the formula (I) in which $R_1$ and $R_2$ have the above-mentioned preferred meanings, $R_3$ and $R_5$ are each carbalkoxy with up to 5 carbon atoms or $R_3$ and $R_5$ together form a —CO-NR-CO— grouping, wherein R is hydrogen, alkyl with 1 to 4 carbon atoms or a phenyl or benzyl radical which is optionally substituted by methyl or chlorine, and $R_4$ and $R_6$ are each hydrogen or chlorine. X, Y and Z are each preferably oxygen and Hal is preferably chlorine.

The process according to the invention is distinguished by a number of advantages. Amongst these, its broad applicability and ease of industrial implementation should be mentioned in particular. A further advantage is the ready availability of the requisite starting materials. Further advantages to be mentioned are the high purity and the good yield of the products obtainable in accordance with the process of the invention.

If, for example, O,O,O-trimethylphosphoric acid ester, chlorine and vinyl chloride are used as starting materials, the course of the reaction in accordance with the present process can be represented by the following equation:

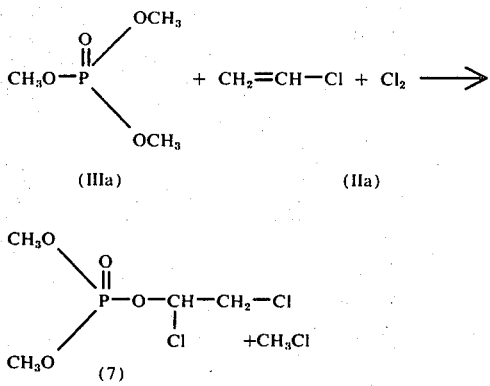

The following compounds may be mentioned as examples of the olefinic starting compounds of the formula (II), to be reacted in accordance with the process: branched and unbranched alkenes such as ethylene, propylene, 1-butene, 2-butene, isobutene, 1-hexene, 1-dodecene, tripropylene, tetrapropylene, tetraisobutene, 1-octene, 1-octadecene, 1-phenyl-3,3,4,4-tetrafluoro-cyclo-butene, cyclopentene, cyclohexane, cyclooctene, cyclododecene, styrene, α-methylstyrene, α- and β-pinene and camphene; diolefins such as 1,3-butadiene, isoprene, 2,3-dimethyl-1,3-butadiene, vinylcyclohexene and 1,4-cyclooctadiene; halogenolefins such as allyl chloride, methallyl chloride, vinyl chloride, 1- and 2-chloropropene, 1,4- and 3,4-dichloro-2-butene, vinyl bromide, allyl bromide, vinyl fluoride, 1,1-dichloroethylene, 1,1-difluoroethylene, trifluoromonochloroethylene and 1- and 3-chlorocyclohexene; unsaturated carboxylic acid derivatives such as, for example, the esters, monoalkylamides, dialkylamides, chlorides and nitriles of acrylic acid, methacrylic acid, crotonic acid, β,β-dimethylacrylic acid, β-chloroacrylic acid, β,β-dichloroacrylic acid, vinylacetic acid, undecenoic acid, oleic acid, linoleic acid, cyclohexene-1-and-3-carboxylic acids, maleic acid, itaconic acid and fumaric acid; and the esters and ethers of unsaturated alcohols, for example of allyl alcohol, 1,4-butenediol and methylene-1,3-propanediol, as well as unsaturated ethers such as ethyl vinyl ether and butyl vinyl ether and unsaturated esters such as vinyl acetate and isopropenyl acetate and 1,3-dioxolen-2-one. It is also possible to use isocyanates and isocyanide-dichlorides with olefinic groupings, for example allyl isocyanate and allyl isocyanide-dichloride, 4-chlorobutenyl isocyanate and isocyanide-dichloride, and isopropenyl isocyanate, as well as ketones and sulfones with olefinic groupings such as methyl vinyl ketone, mesityl oxide, phenyl vinyl sulfone, sulfolene and 3-methylsulfolene, as well as olefinic sulfonic acid derivatives, for example α-chlorovinyl, allyl, methylallyl, vinyl and β,β-dimethylvinyl sulfochlorides.

The following compounds may be mentioned as examples of starting materials of the formula (III) to be reacted in accordance with the process: O,O,O-trimethyl-, O,O,O-triethyl-O,O,O-tris-(2-chloro-ethyl)-, O,O,O-tri-n-butyl-, O,O,O-tris(2-ethyl-hexyl)-, O,O-dimethyl-O-1,2-dichloroethyl-, O,O-dimethyl-O-tetrachloroethyl-, O,O-dimethyl-O-[3-chloroprop(2)-yl]-, O,O,O-trimethylthiono- and O,O,O-triethylthionophosphoric acid esters, dithiophosphoric acid O,O,S-trimethyl and O,O,S-triethyl esters, trithiophosphoric acid O,S,S-trimethyl ester, methanephosphonic acid dimethyl ester, diethyl ester and dibutyl ester and cyclohexanephosphonic acid dimethyl ester.

The process according to the invention is preferably carried out in the presence of a solvent or diluent. As such it is possible to use either an excess of the (thio)phosphoric (phosphonic) acid ester (III) - provided it is liquid under the reaction conditions - or inert organic solvents, especially chlorinated hydrocarbons, such as chloroform or chlorobenzene, or ethers, such as diethyl ether and dibutyl ether and dioxane.

The reaction temperature can be varied within a fairly wide range. In general, the reaction is carried out between about −50°C and +120°C, preferably between about −10°C and +100°C and especially at about −10°C to +50°C.

The reaction is in general allowed to take place under normal pressure.

The halogenating agents employed are preferably elementary chlorine or bromine, or sulfuryl chloride.

Furthermore, in order to achieve good yields, the reaction is preferably carried out using equivalent amounts of halogenating agent and at least equivalent amounts of (thio)-phosphoric or phosphonic acid ester (III), relative to the olefinic reactant (II). Particularly good yields are often obtained when using an excess of reactant (III), say in the molar ratio of about 1:1 to 5:1 relative to reactant (II).

Preferably, the (thio)phosphoric(phosphonic) acid ester (III), optionally in one of the above-mentioned solvents or diluents, is taken first and the halogenating agent and the olefin component (II) are added simultaneously to this solution at the stated temperatures, the internal temperature of the mixture being regulated by external cooling. After the reaction has subsided, the batch is stirred for some time longer while warming, preferably to about 40°C–100°C, to complete the reaction. The reaction mixture is then cooled to room temperature and worked up in accordance with customary methods.

In some cases it is advantageous to add to the reaction mixture small amounts of Friedal-Crafts catalysts such as iron(III) chloride, zinc chloride or aluminum chloride.

The products of the process, which in most cases have not previously been described in the literature, are mostly obtained in the form of colorless to pale yellow-colored water-insoluble oils which can be distilled, without decomposition, under reduced pressure and can be purified in this way. The boiling points can be used to characterize the new compounds. In some cases, the products of the process are first obtained as mixtures of different isomers or homologues, but these can be separated by fractional distillation.

As already mentioned above, the (thio)phosphoric-(phosphonic) acid esters which can be prepared in accordance with the present process may be used as flameproofing agents. In addition, they can also be used as plasticizers in plastics. Thus, when added to cellulose acetate molding powders to about 2 to 5% by weight they function as both plasticizers and flame-proofing agents.

The examples which follow illustrate the process according to the invention.

EXAMPLE 1

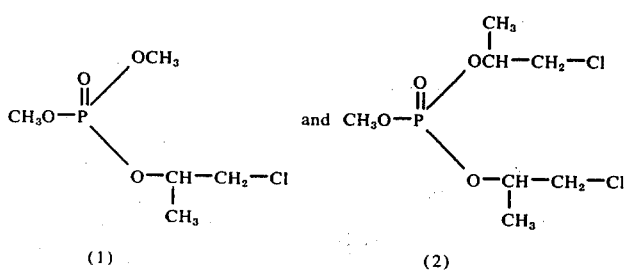

40 g of chlorine and 65 g of propylene were passed simultaneously into 250 g of O,O,O-trimethylphosphoric acid ester at −5° to 0°C; during the reaction, the mixture was cooled and stirred. On subsequently warming the reaction mixture to about 50°C, excess propylene and methyl chloride were evolved. Fractional distillation gave 62 g (54% of theory) of O,O-dimethyl-O-[3-chloro-prop(2)-yl]-phosphoric acid ester of boiling point 70° to 73°C/0.15 mm Hg and about 6 g of O-methyl-O,O-bis-[3-chloro-prop(2)-yl]-phosphoric acid ester of boiling point 105° to 110°C/0.15 mm Hg.

EXAMPLE 2

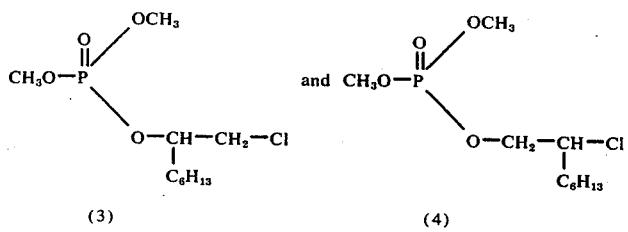

56 g of octene-1 were added dropwise to 250 g of O,O,O-trimethylphosphoric acid ester at −10° to 0°C and 35 g of chlorine were passed in at the same time. After completion of the reaction, the mixture was warmed to room temperature, during which methyl chloride was evolved. The subsequent fractional distillation of the reaction mixture gave 91 g (71% of theory) of an isomer mixture of O,O-dimethyl-O-[1-hexyl-2-chloroethyl]-phosphoric acid ester (about 70%) and O,O-dimethyl-O-[2-chloro-2-hexylethyl]-phosphoric acid ester (about 30%) of boiling point 121° to 128°C/0.5 mm Hg.

EXAMPLE 3

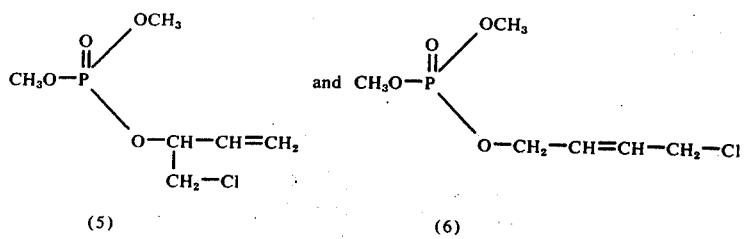

A further 56 g of butadiene and 62 g of chlorine were passed simultaneously into a solution of 56 g of 1,3-butadiene in 645 g of O,O,O-trimethylphosphoric acid ester at 0°C. During the reaction, the mixture was stirred and cooled, and it was subsequently fractionally distilled under reduced pressure. This gave 116 g (62% of theory) of O,O-dimethyl-O-[4-chloro-1-buten-3(yl)]-phosphoric acid ester of boiling point 78°C/0.15 mm Hg and 23 g (12% of theory) of O,O-dimethyl-O-[1-chloro-2-buten-(4)yl]-phosphoric acid ester of boiling point 102° to 105°C/0.2 mm Hg.

EXAMPLE 4

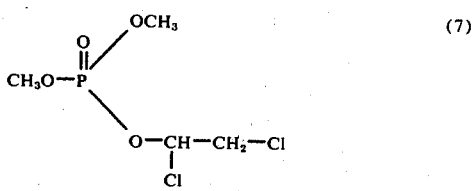

40 g of vinyl chloride and 35 g of chlorine were passed into 250 g of O,O,O-trimethylphosphoric acid ester, in which 0.5 g of iron(III) chloride had been dissolved, at −5°C to +5°C, while stirring and cooling. After completion of the reaction, the reaction mixture was heated to 60°C, during which the methyl chloride produced during the reaction was evolved as a gas, simultaneously with excess vinyl chloride.

Fractional distillation of the residual product under reduced pressure gave 95 g (86% of theory) of O,O- dimethyl-O-[1,2-dichloroethyl]-phosphoric acid ester of boiling point 85° to 87°C/0.2 mm Hg.

EXAMPLE 5

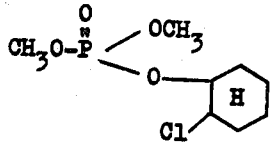
(8)

41 g of cyclohexene were dissolved in 250 g of O,O,O-trimethylphosphoric acid ester and 35 g of chlorine were then passed into the solution while cooling at about 10°C. On warming the reaction mixture after completion of the reaction, methyl chloride was evolved. The subsequent fractional distillation gave 75 g (62% of theory) of O,O-dimethyl-O-[2-chlorocyclohexyl]-phosphoric acid ester of boiling point 113° to 115°C/0.2 mm Hg.

EXAMPLE 6

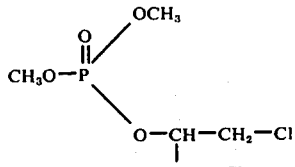 and 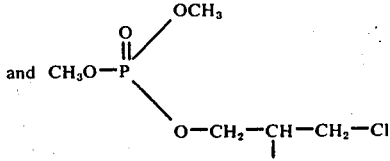

(9)    (10)

38.5 g of allyl chloride and 35 g of chlorine were added simultaneously to 250 g of O,O,O-trimethylphosphoric acid ester at about −5°C. On warming the reaction mixture to 60°C, methyl chloride was evolved. The subsequent fractional distillation gave an isomer mixture of O,O-dimethyl-O-[1,3-dichloro-prop(2)yl]- and O,O-dimethyl-O-[2,3-dichloro-prop(1)yl]-phosphoric acid ester of boiling point 100° to 105°C/0.2 mm Hg. The yield was 86% of theory.

EXAMPLE 7

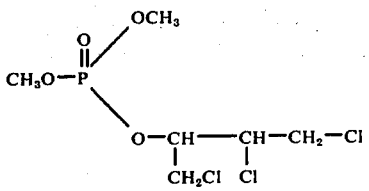
(11)

35 g of chlorine were passed into a solution of 63 g of 3,4-dichloro-2-butene in 250 g of O,O,O-trimethylphosphoric acid ester at 0°C, while cooling. The fractional distillation of the reaction mixture gave 84 g (60% of theory) of O,O-dimethyl-O-[1,3,4-trichlorobut(2)yl]-phosphoric acid ester of boiling point 137° to 140°C/0.2 mm Hg.

EXAMPLE 8

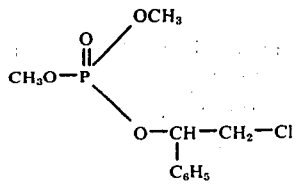
(12)

52 g of styrene and 35 g of chlorine were metered simultaneously into 250 g of O,O,O-trimethylphosphoric acid ester at −5°C. After completion of the reaction, the batch was fractionally distilled. 76 g (58% of theory) of O,O-dimethyl-O-[1-phenyl-2-chloroethyl]-phosphoric acid ester of boiling point 129° to 131°C/0.35 mm Hg were obtained.

EXAMPLE 9

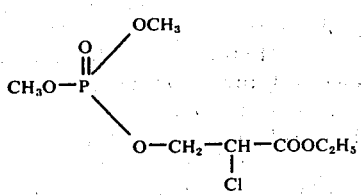
(13)

50 g of acrylic acid ethyl ester were added dropwise to 250 g of O,O,O-trimethylphosphoric acid ester and at the same time 35 g of chlorine were passed in, while keeping the reaction temperature at 0° to 20°C. After completion of the reaction, the mixture was warmed, whereupon methyl chloride was evolved. The fractional distillation of the reaction mixture gave 65 g (50% of theory) of O,O-dimethyl-O-[2-chloro-2-carbethoxy-ethyl]-phosphoric acid ester of boiling point 116° to 119°/0.1 mm Hg.

EXAMPLE 10

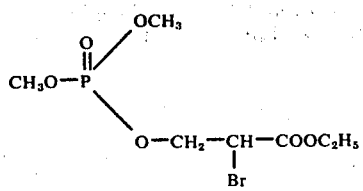
(14)

50 g of acrylic acid ethyl ester were dissolved in 250 g of O,O,O-trimethylphosphoric acid ester. 80 g of bromine were added dropwise to this solution, while stirring and cooling. On subsequent warming to about 50°C, methyl bromide was evolved. The subsequent distillation under reduced pressure gave 53 g (35% of theory) of O,O-dimethyl-O-[2-bromo-2-carbethoxyethyl]-phosphoric acid ester boiling at 125°C/0.4 mm Hg.

EXAMPLE 11

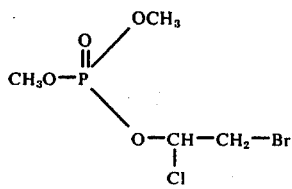 (15)

70 g of gaseous vinyl chloride were passed into 250 g of O,O,O-trimethylphosphoric acid ester to which 0.5 g of iron (III) chloride had been added, at about 0°C, and at the same time 160 g of bromine were added dropwise. On warming the reaction mixture after the reaction, methyl bromide was evolved. The fractional distillation gave 151 g (57% of theory) of O,O-dimethyl-O-[1-chloro-2-bromoethyl]-phosphoric acid ester of boiling point 93° to 95°C/0.2 mm Hg.

Example 12

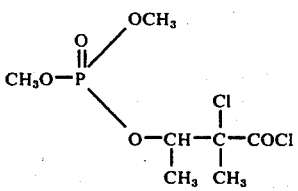 (16)

59 g of 2-methyl-crotonic acid chloride and 35 g of chlorine were metered simultaneously into 250 g of O,O,O-trimethylphosphoric acid ester while keeping the reaction temperature at −10° to 0°C by external cooling of the mixture. After warming the batch to 50°C, the excess trimethylphosphate was separated off by thin layer evaporation and the crude reaction product (80 g) was then fractionally distilled under reduced pressure. 62 g (45% of theory) of O,O-dimethyl-O-[3-chloro-3-chlorocarbonyl-but(2)yl]-phosphoric acid ester of the above formula, of boiling point 124° to 127°C/0.3 mm Hg were obtained.

EXAMPLE 13

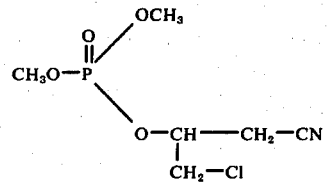 (17)

33.5 g of allyl cyanide and 35 g of chlorine were added simultaneously to 250 g of O,O,O-trimethylphosphoric acid ester while keeping the reaction temperature of the mixture at −5°C by cooling. The reaction mixture was then fractionally distilled. Methyl chloride was first evolved and then excess trimethyl phosphate and low-boiling-point by-products were distilled off. The crude product, of the above formula, which remained was subsequently purified by thin-layer evaporator distillation. 67 g (62% of theory) of pure O,O-dimethyl-O-[1-chloro-3-cyano-prop(2)yl]-phosphoric acid ester of boiling point 120° to 122°C/0.2 mm Hg were obtained.

EXAMPLE 14

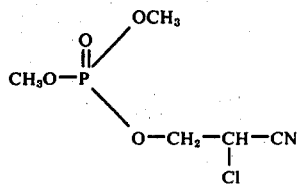 (18)

26.5 g of acrylonitrile were dissolved in 250 g of O,O,O-trimethylphosphoric acid ester and 35 g of chlorine were passed in at 20°C. After 10 hours, the solution was worked up by fractional distillation. O,O-dimethyl-O-[2-chloro-2-cyanoethyl]-phosphoric acid ester was obtained as a fraction of boiling point 95° to 98°C/0.1 mm Hg. The yield was 6.5 g (6% theory).

EXAMPLE 15

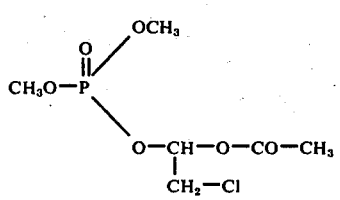 (19)

43 g of vinyl acetate and 35 g of chlorine were reacted with 250 g of O,O,O-trimethylphosphoric acid ester at 0°C. The fractional distillation of the reaction mixture gave 47 g (38% of theory) of O,O-dimethyl-O-[1-acetoxy-2-chloroethyl]-phosphoric acid ester of boiling point 116° to 118°C/0.7 mm Hg.

EXAMPLE 16

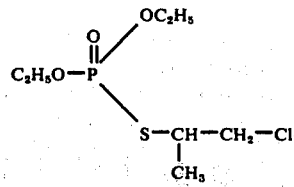 (20)

35 g of chlorine and 40 g of propylene were added simultaneously to 250 g of O,O,O-triethylthionophosphoric acid ester at −5°C. After the reaction, the reaction mixture was distilled under reduced pressure. 12 g (10% of theory) of O,O-diethyl-S-[3-chloro-prop(-2)yl]-thiolphosphoric acid ester of boiling point 83° to 85°C/0.15 mm Hg were obtained.

EXAMPLE 17

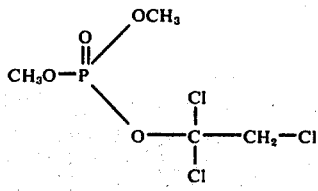 (21)

49 g of 1,1-dichloro-ethylene were dissolved in 250 g of O,O,O-trimethylphosphoric acid ester and 0.5 g of iron(III) chloride were added to this solution. 35 g of chlorine were then passed into the mixture at 0°C. After completion of the reaction, the reaction mixture was fractionally distilled. 70 g (55% of theory) of O,O-dimethyl-O -[1,1,2-trichloroethyl]-phosphoric acid ester of boiling point 89° to 90°C/0.2 mm Hg were obtained.

EXAMPLE 18

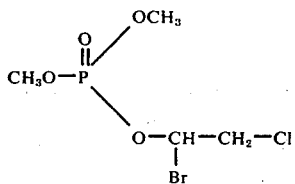

35.5 g of chlorine were passed into a solution of 53.5 g of vinyl bromide in 250 g of O,O,O-trimethylphosphoric acid ester while cooling and stirring at 0°C. The mixture was then degassed by applying a vacuum while warming to 50°C, was was then fractionally distilled. 95 g (71% of theory) of O,O-dimethyl-O-[1-bromo-2-chloroethyl]-phosphoric acid ester of boiling point 94° to 96°C/0.6 mm Hg were obtained.

EXAMPLE 19

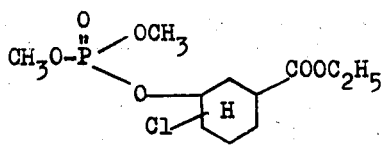

35 g of chlorine were passed into a solution of 77 g of 3-cyclohexene-1-carboxylic acid ethyl ester in 250 g of O,O,O-trimethylphosphoric acid ester at −8°C. The resulting reaction product was then fractionally distilled. 78 g (50% of theory) of a O,O-dimethyl-O-[chloro-carbethoxy-cyclohexyl]-phosphoric acid ester of boiling point 144° to 149°C/0.3 mm Hg were obtained.

EXAMPLE 20

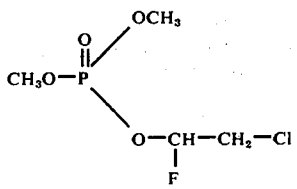

35 g of chlorine and 70 g of vinyl fluoride were passed simultaneously into 250 g of O,O,O-trimethylphosphoric acid ester while stirring and cooling at −20°C. After completion of the reaction, methyl chloride and vinyl fluoride which were still in solution were removed by warming the mixture to 50°C and the batch was then fractionally distilled. 99 g (97% of theory) of O,O-dimethyl-O-[1-fluoro-2-chloroethyl]phosphoric acid ester of boiling point 76° to 77°C/0.4 mm Hg were obtained.

EXAMPLE 21

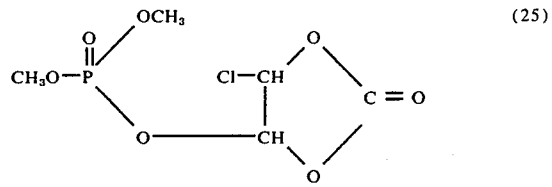

43 g of 1,3-dioxolen-2-one were added dropwise to 250 g of O,O,O-trimethylphosphoric acid ester and 35 g of chlorine were passed in at the same time. The temperature of the mixture was kept at −10°C to 0°C during the reaction by external cooling, methyl chloride was then expelled by warming the batch and the reaction mixture was worked up by fractional distillation. 105 g (86% of theory) of 4-chloro-5-[O,O-dimethyl-phosphoryl]-1,3-dioxolan-2-one of the above formula and of boiling point 120° to 122°C/0.2 mm Hg were obtained.

It will be appreciated that the instant specification and examples are set forth by way of illustration and not limitation, and that various modifications and changes may be made without departing from the spirit and scope of the present invention.

What is claimed is:

1. A process for the preparation of a (thio)-phosphoric (phosphonic) acid ester of the formula

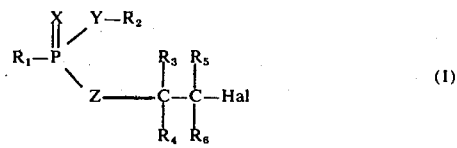

in which
$R_1$ is a straight-chain or branched alkyl, alkylmercapto or alkoxy group with up to 8 carbon atoms,
$R_2$ is alkyl with 1 to 8 carbon atoms optionally substituted by chlorine,
$R_4$ and $R_6$ each individually is hydrogen, $C_1$-$C_4$-alkyl or halogen.
X, Y and Z each individually is oxygen or sulfur,
Hal is chlorine or bromine, and
$R_3$ and $R_5$ each individually is hydrogen; halogen; a $C_1$-$C_{18}$-alkyl, acyloxy or $C_2$-$C_{12}$-alkenyl radical which can be substituted by halogen, an acyloxy or alkoxy group with up to 18 carbon atoms, isocyano, dichloroisocyano, chlorocarbonyl, cyano, chlorosulfonyl, a carbalkoxy group with up to 8 carbon atoms in the alkoxy moiety, or an optionally substituted carbamino group with up to 12 carbon atoms; phenyl; halogen-substituted phenyl; or $C_1$-$C_4$-alkyl-substituted phenyl; or
$R_3$ and $R_5$ together form a 4- to 12-membered aliphatic or heterocyclic ring, or
$R_5$ may alternatively be chlorocarbonyl; cyano; a carbalkoxy or an optionally substituted carbamino group with up to 9 carbon atoms; an alkylcarbonyl, alkylsulfonyl, arylcarbonyl or arylsulfonyl group, each with up to 7 carbon atoms; or an aldehyde group, which comprises reacting at a temperature of about −50°C to 120°C an olefin of the formula

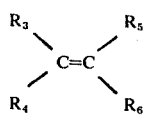
(II)

in a one-step process with a halogenating agent and at least an equivalent amount of a (thio)phosphoric (phosphonic) acid ester of the formula

(III)

2. A process according to claim 1, in which $R_1$ is alkyl or alkoxy with 1 to 6 carbon atoms, and $R_2$ is optionally chlorine-substituted alkyl with 1 to 6 carbon atoms.

3. A process according to claim 2, in which $R_1$ is methyl, methoxy, or ethoxy and $R_2$ is methyl or ethyl.

4. A process according to claim 1, in which $R_3$ and $R_5$ each individually is hydrogen; fluorine, chlorine; bromine; or acyloxy with up to 5 carbon atoms, or alkyl or alkenyl with 1 to 6 carbon atoms optionally substituted by chlorine, bromine, isocyano, dichloroisocyano, chlorocarbonyl, cyano, chlorosulfonyl, a carbalkoxy, acyloxy or alkoxy group containing up to 5 carbon atoms, or an alkylated carbamino group.

5. A process according to claim 1, in which the radicals $R_3$ and $R_4$ are fluorine or chlorine.

6. A process according to claim 1, in which $R_3$ and $R_5$ together form a 5-membered or 6-membered ring which contains oxygen, a carbonyl group or a sulfone group, in addition to carbon atoms, as ring members and $R_4$ and $R_6$ each independently is hydrogen, chlorine or methyl.

7. A process according to claim 2, in which $R_3$ and $R_5$ each independently is carbalkoxy with up to 5 carbon atoms and $R_4$ and $R_6$ each independently is hydrogen or chlorine.

8. A process according to claim 1, in which the starting material of the formula (III) is an O,O,O-trialkyl-phosphoric acid ester.

9. A process according to claim 1, in which the starting material of the formula (III) is an O,O,O-trialkylthionophosphoric acid ester.

10. A process according to claim 1, in which the reaction is carried out at about −10°C to 50°C.

11. A process according to claim 1, in which the reaction is effected in the presence of a solvent or diluent.

12. A process according to claim 11 in which an excess of the (thio)phosphoric(phosphonic) acid ester (III) is used as the solvent or diluent.

13. A process according to claim 1, in which the halogenating agent is elementary chlorine or bromine, or sulfuryl chloride.

14. A process according to claim 1, in which between 1 and 5 moles of (thio)phosphoric(phosphonic) acid ester (III) are used per mole of the olefinic reactant (II).

15. A process according to claim 1, in which a Friedel-Crafts catalyst is added to the reaction mixture.

16. A process according to claim 15, in which the Friedel-Crafts catalyst is iron(III) chloride, zinc chloride or aluminum chloride.

17. A process according to claim 4, in which $R_1$ is methyl, methoxy, or ethoxy and $R_2$ is methyl or ethyl, the reaction is effected at a temperature of about −10° to 50°C in the presence of a solvent or diluent, between 1 and 5 moles of (thio)phosphoric(phosphonic) acid ester (III) are used per mole of the olefinic reactant (II), the halogenating agent is elementary chlorine or bromine or sulfuryl chloride, and at least one of iron (III) chloride, zinc chloride and aluminum chloride is added to the reaction mixture.

* * * * *